United States Patent [19]

Lee et al.

[11] Patent Number: 4,551,533
[45] Date of Patent: Nov. 5, 1985

[54] ANTIBIOTIC LL-D42067α

[75] Inventors: Taikwang M. Lee, Holmdel, N.J.; Donald B. Borders, Suffern; Joseph J. Goodman, Spring Valley, both of N.Y.; Raymond T. Testa, Cedar Grove; William M. Maiese, Bridgewater, both of N.J.; David P. Labeda, Peoria, Ill.

[73] Assignee: American Cyanamid Company, Stamford, Conn.

[21] Appl. No.: 593,160

[22] Filed: Mar. 26, 1984

[51] Int. Cl.⁴ .................. C07D 521/00; C12P 17/18; C12R 1/03; C12N 1/20

[52] U.S. Cl. .................. 546/35; 435/118; 435/253; 546/34

[58] Field of Search .............. 546/35, 34; 435/253

[56] References Cited

U.S. PATENT DOCUMENTS 4,407,946 10/1983 Labeda et al. ............... 435/75

Primary Examiner—Alan L. Rotman
Attorney, Agent, or Firm—Anne M. Rosenblum; Susan H. Rauch

[57] ABSTRACT

Antibiotic LL-D42067α derived by aerobic fermentation of the microorganism *Actinomadura madurae* subspecies simaoensis NRRL 15734, useful as an antibacterial and antiparasitic agent.

1 Claim, 5 Drawing Figures

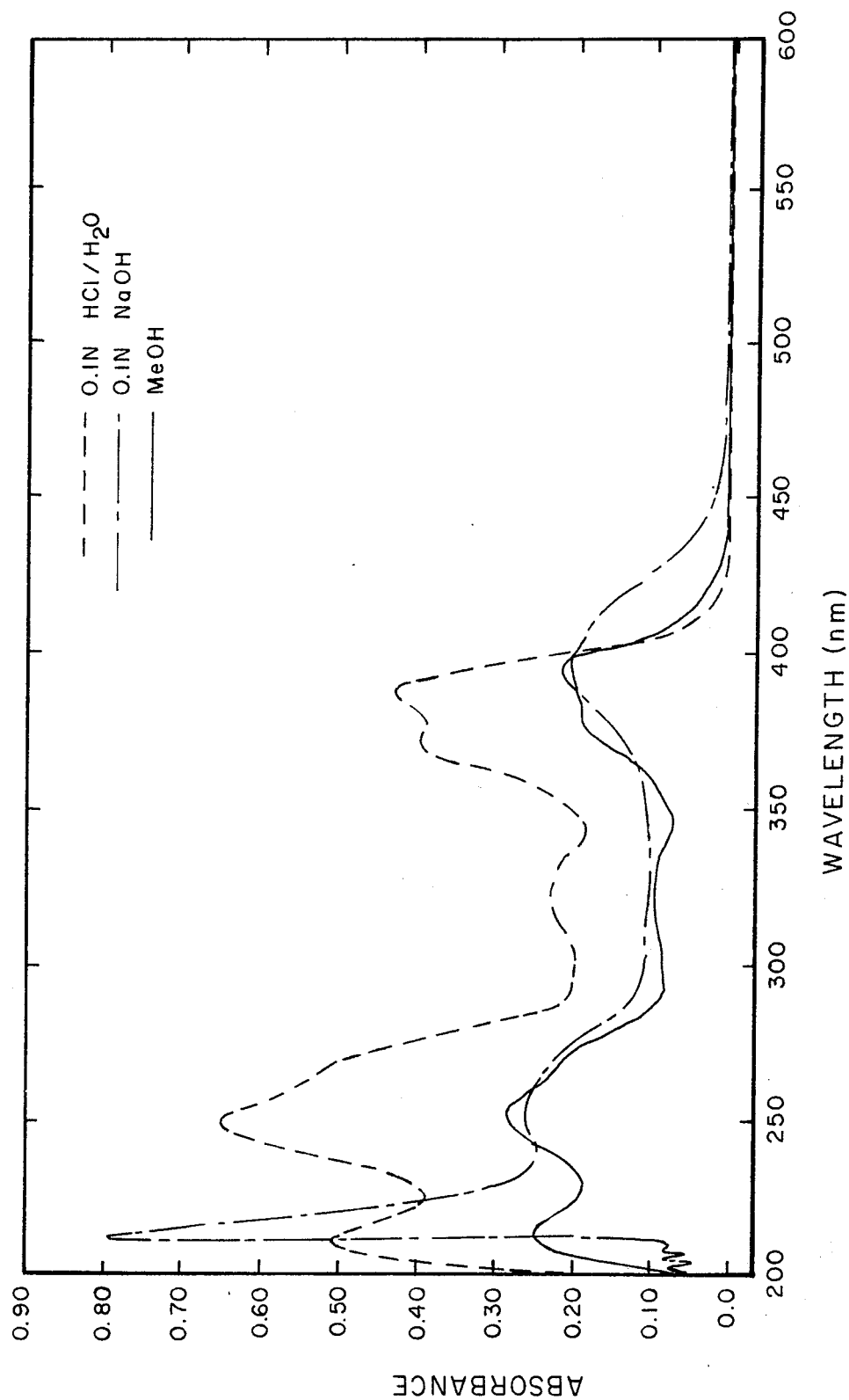
FIGURE I

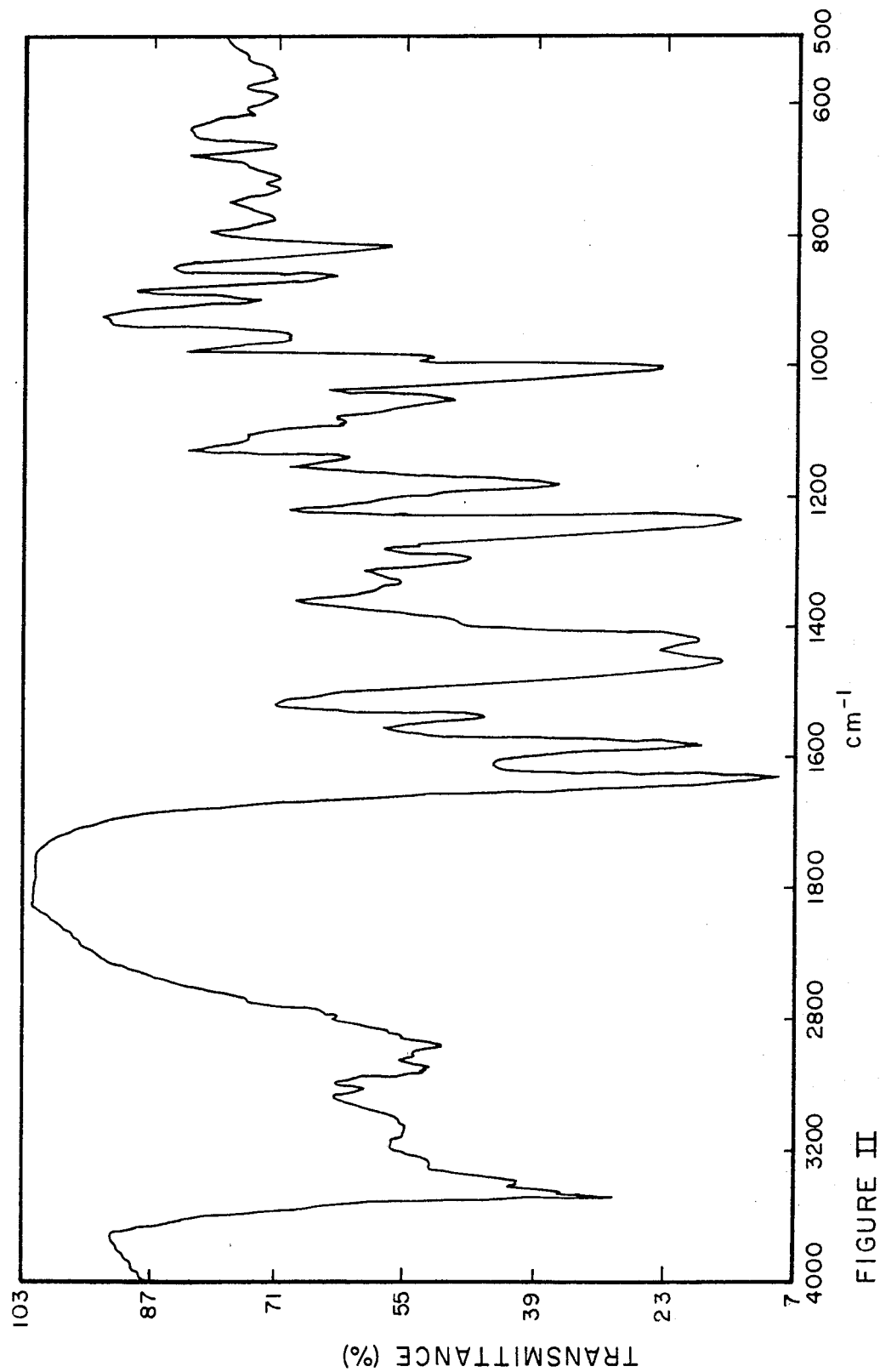

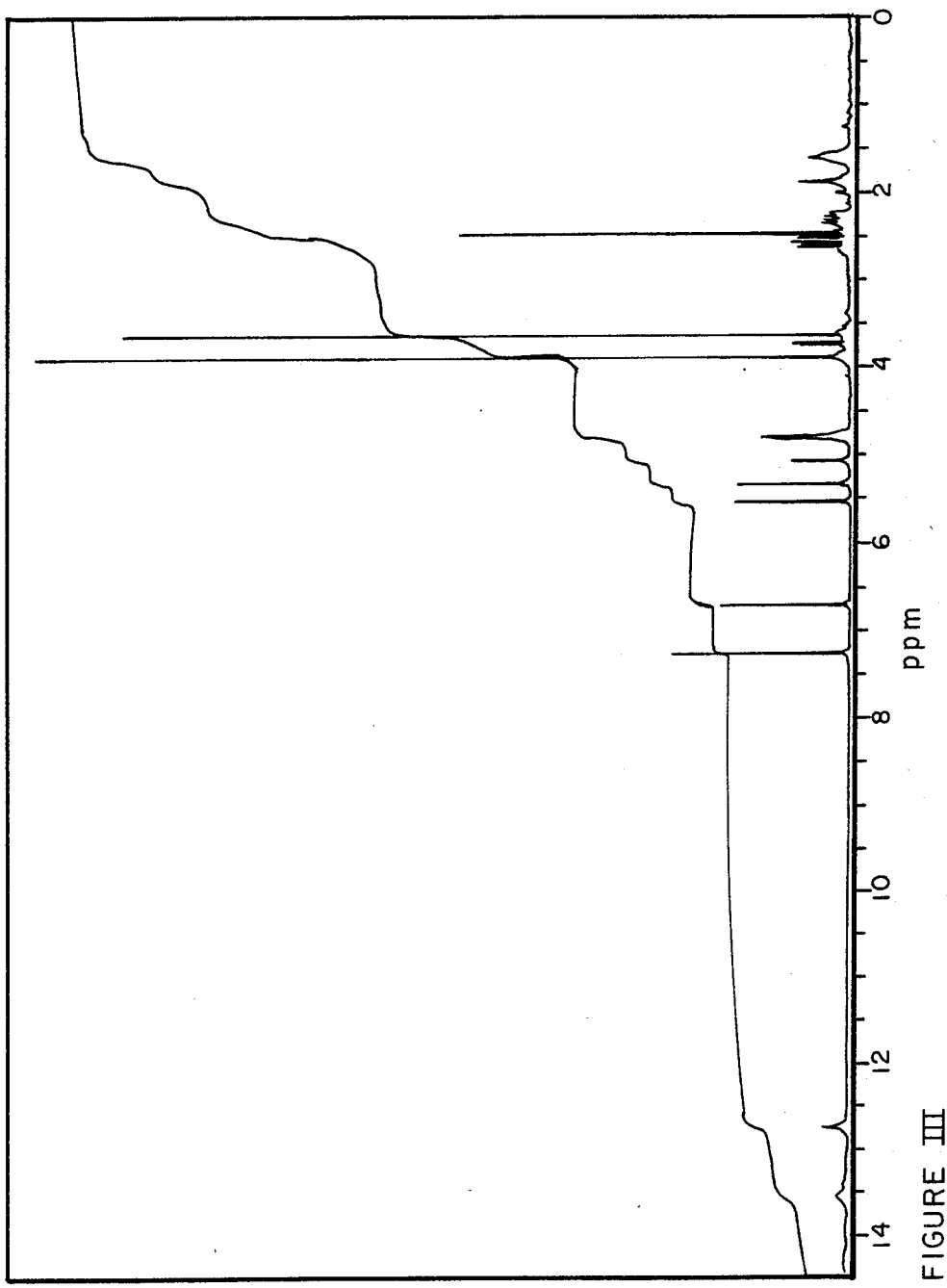
FIGURE III

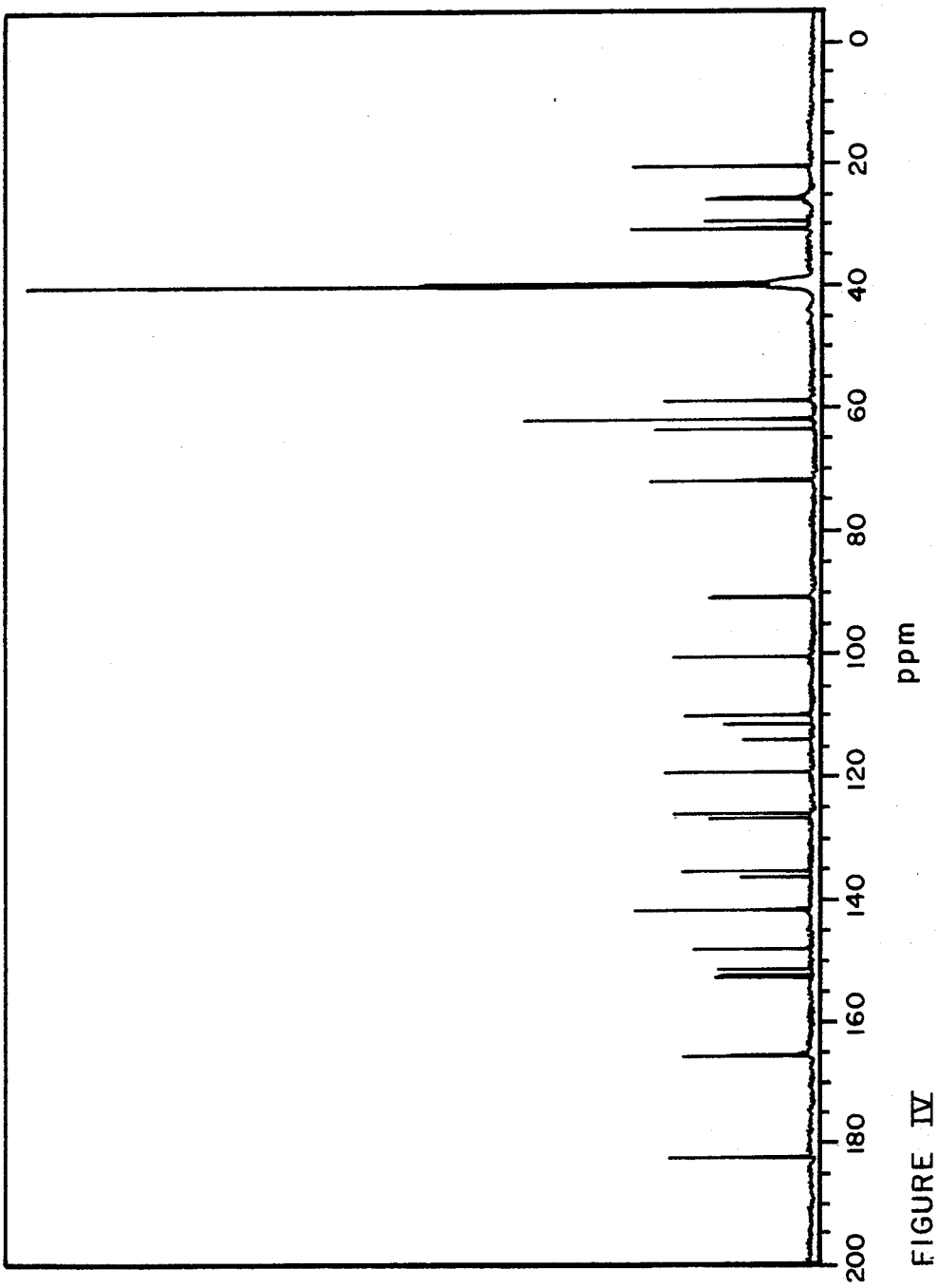
FIGURE IV

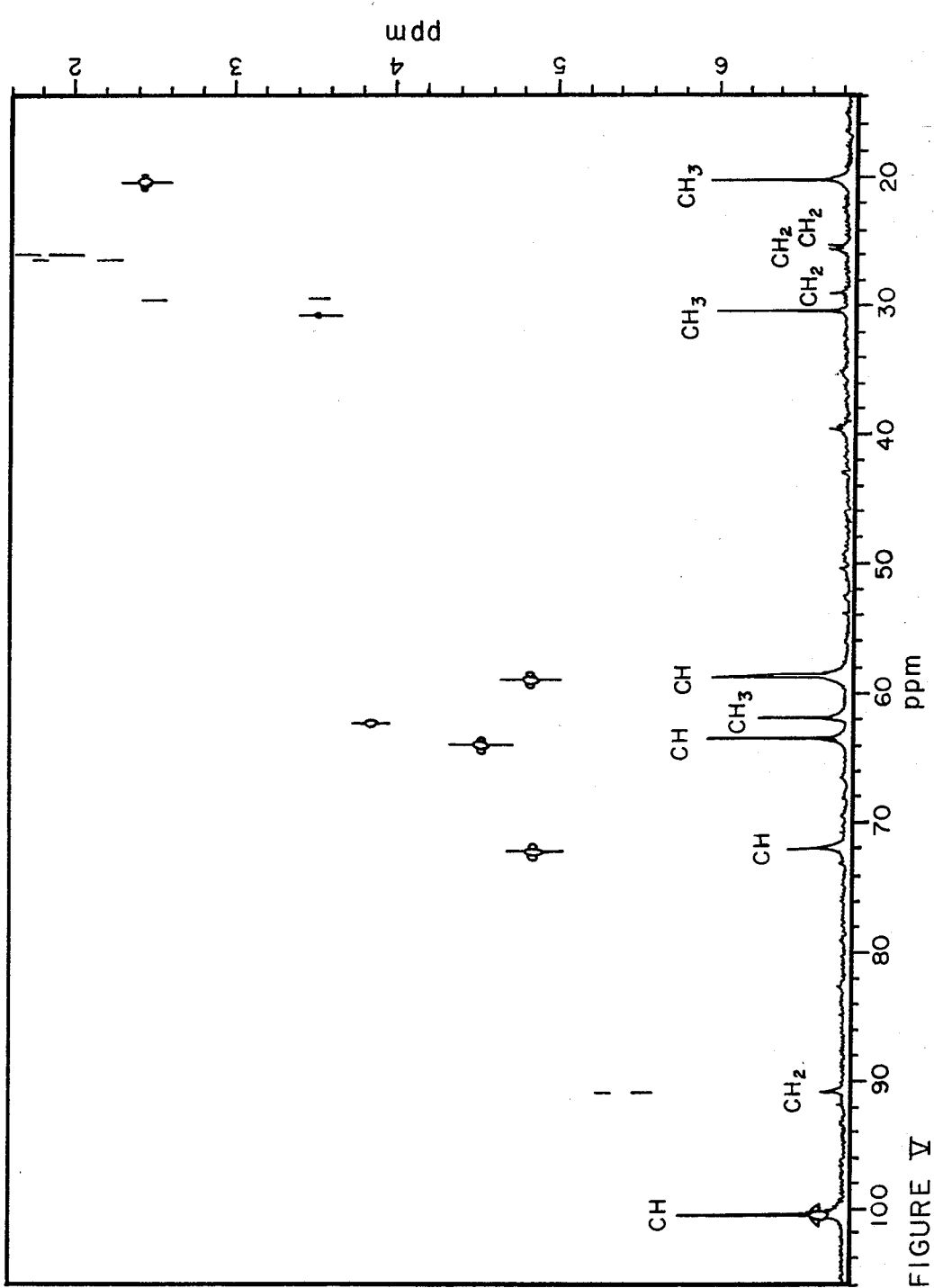
FIGURE V

ANTIBIOTIC LL-D42067α

SUMMARY OF THE INVENTION

This invention relates to a new antibacterial and antiparasitic agent designated LL-D42067α, to its production by fermentation, to methods for its recovery and concentration from crude solutions and to processes for its purification. The present invention includes within its scope the biologically pure culture of the antibiotic.

The structure and relative stereochemistry of LL-D42067α have been elucidated by X-ray crystallography, and is shown below.

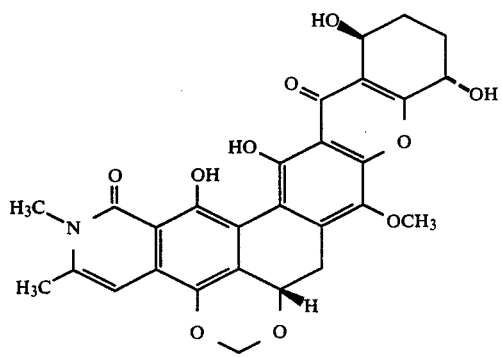

The physico-chemical characteristics of LL-D42067α are described below:

(1) Molecular weight: 535 (FAB-MS);
(2) Molecular formula: $C_{28}H_{25}NO_{10}$;
(3) Specific optical rotation: $[\alpha]_D^{26} = +836^{30} - 40°$ (C 0.3, DMF);
(4) Ultraviolet absorption spectra: as shown in FIG. I
   $UV_{MAX}^{CH3OH} = 215$ nm ($\epsilon$ 13,200); 254 nm ($\epsilon$ 15,000); 320 nm ($\epsilon$ 5,100); 395 nm ($\epsilon$ 11,400);
   $UV_{MAX}^{0.1\ N\ HCl} = 213$ nm ($\epsilon$ 27,100); 253 nm ($\epsilon$ 34,500); 321 nm ($\epsilon$ 12,200); 374 nm ($\epsilon$ 21,100); 389 nm ($\epsilon$ 22,900);
   $UV_{MAX}^{0.1\ N\ NaOH} = 217$ nm ($\epsilon$ 42,100); 253 nm ($\epsilon$ 13,900); 312 nm ($\epsilon$ 5,700); 395 nm ($\epsilon$ 10,700);
(5) Infrared absorption spectrum: as shown in FIG. II (KBr disc): 1650, 1598, 1543, 1470, 1440, 1260, 1195, 1020 cm$^{-1}$;
(6) Proton nuclear magnetic resonance spectrum (CDCl$_3$): as shown in FIG. III, and described in Table I;
(7) Carbon-13 nuclear magnetic resonance spectrum (DMSO): as shown in FIG. IV and described in Table II; and
(8) Proton to carbon-13 chemical shift correlation map (DMSO): as shown in FIG. V.

TABLE I

| δ* | Proton NMR Data for LL-D42067α | | J (H) |
|---|---|---|---|
| | No. of Hydrogen** | Multiplicity*** | |
| 1.88 | 2 | m | |
| 2.34 | 2 | m | |
| 2.45 | 3 | s | |
| 2.58 | 1 | m | |
| 3.62 | 3 | s | |
| 3.72 | 1 | d,d | 4.64, 14.22 |
| 3.88 | 3 | s | |
| 4.80 | 2 | m | |
| 5.08 | 1 | m | |
| 5.32 | 1 | d | 5.81 |
| 5.55 | 1 | d | 5.81 |
| 6.70 | 1 | s | |
| 12.76 | 1 | s | |
| 13.58 | 1 | s | |

*CDCl$_3$, ppm downfield from TMS.
**Spectrum in DMSO-d$_6$, shows two additional absorptions at 4.55(s) and 5.91 (d) ppm.
***s = singlet; d = doublet; t = triplet; m = multiplet.

TABLE II

| Carbon | Carbon-13 NMR Data for LL-D42067α | |
|---|---|---|
| | Chemical Shift (ppm)* | Carbon Type |
| 1 | 20.4 | CH$_3$ |
| 2 | 25.4 | CH$_2$ |
| 3 | 25.8 | CH$_2$ |
| 4 | 29.0 | CH$_2$ |
| 5 | 30.4 | CH$_3$ |
| 6 | 58.5 | CH |
| 7 | 61.6 | CH$_3$ |
| 8 | 63.3 | CH |
| 9 | 71.7 | CH |
| 10 | 90.4 | CH$_2$ |
| 11 | 100.0 | CH |
| 12 | 109.2 | q** |
| 13 | 109.7 | q |
| 14 | 111.0 | q |
| 15 | 113.7 | q |
| 16 | 119.0 | q |
| 17 | 125.8 | q |
| 18 | 126.6 | q |
| 19 | 134.9 | q |
| 20 | 135.3 | q |
| 21 | 136.1 | q |
| 22 | 141.3 | q |
| 23 | 147.9 | q |
| 24 | 151.1 | q |
| 25 | 152.5 | q |
| 26 | 165.4 | q |
| 27 | 165.6 | q |
| 28 | 182.3 | q |

*DMSO-d$_6$, ppm downfield from TMS.
**q = quarternary.

DETAILED DESCRIPTION OF THE INVENTION

The new antibacterial agent designated LL-D42067α, is formed during the cultivation under controlled conditions of a new strain of a new subspecies of *Actinomadura madurae*. This new strain is maintained in the culture collection of the Medical Research Division, American Cyanamid Company, Pearl River, N.Y. as culture number LL-D42067. A viable culture of this new microorganism has been deposited with the Patent Culture Collection Laboratory, Northern Regional Research Center, U.S. Department of Agriculture, Peoria, Ill. 61604, and has been added to its permanent collection. It is freely available to the public in this depository under its accession number NRRL 15734.

Culture LL-D42067 was isolated from a soil sample from San Simao, Brazil. The culture was taxonomically characterized and was identified as a new subspecies of *Actinomadura madurae*, designated *Actinomadura madurae* subspecies simaoensis.

Observations were made of the cultural, physiological and morphological features of the culture in accordance with the methods detailed by Shirling and Gottlieb [Intern. J. System. Bacteriol., 16:313–340 (1966)] and Gordon, et al. [Intern. J. System. Bacteriol., 24:54–63 (1974)]. The chemical composition of the cell walls of the culture was determined using the method of Lechevalier, et al. [Adv. Appl. Microbiol., 14:47–72 (1971)]. Details are recorded in Tables III–V, and a general description of the culture is given below. Underscored descriptive colors are taken from Kelly and Judd [Nat. Bur. Stand., Spec. Publ., 440 (1976)] and the accompanying Intersociety Color Council, National Bureau of Standards Centroid Color Charts.

GROWTH CHARACTERISTICS

Table III describes the cultural characteristics of culture LL-D42067 on various agar media which were selected from those recommended by the International Streptomyces Project Committee (hereinafter referred to as "ISP").

MICROMORPHOLOGY

Microscopic examination of the strain showed it to form short chains of conidia on aerial hyphae which were slightly hooked to short-spirals (up to three turns). The spore surfaces were smooth when observed by electron microscopy, distinguishing this isolate from *A. verrucosopora*.

CELL WALL COMPOSITION

Whole cell analyses showed the strain to contain meso diaminopimelic acid (DAP) and the sugar 3-O-methyl-D-galactose (madurose); thus it falls into whole cell pattern type B. The cell wall composition was of the type III (meso DAP, glutamic acid, alanine, muramic acid and glucosamine) and the phospholipid pattern of type PIV (phosphatidyl ethanolamine and/or methylethanolamine plus unknown glucosamine-containing phospholipids). These data support the assignment of the strain to the genus Actinomadura. The PIV phospholipid type is not typical for *A. madurae*, which is usually PI.

PHYSIOLOGICAL REACTIONS

The physiological reactions of strain LL-D42067 were examined using both the ISP system, Shirling and Gottlieb [Intern. J. Syst. Bacteriol., 16:313–340 (1966)] and the Gordon tests, Gordon, et al. [Intern. J. Syst. Bacteriol., 24:54–63 (1974)]. The utilization pattern of the strain of ISP carbohydrate media is given in Table IV, along with those of other members of the genus reacting similarly. Culture LL-D42067 resembles the *Actinomadura madurae* and *Actinomadura verrucosopora* groups. As indicated above, however, it differs from *Actinomadura verrucosopora* in having smooth spore walls. A comparison of reactions in the Gordon test series of *Actinomadura madurae* (Gordon's data; see reference above) and LL-D42067, summarized in Table V, revealed differences only in amylase production and acid from glycerol and raffinose. Since amylase production and raffinose utilization have been found to be variable in *Actinomadura madurae* [Goodfellow, N., et al., J. Gen. Microbiol., 112:95–111 (1979)], the glycerol reaction remains the only physiological difference of LL-D42067 from this taxon.

Since strain LL-D42067 is the same as *Actinomadura madurae* in all properties evaluated except for its glycerol reaction and its PIV phospholipid pattern, it has been assigned to the taxon *Actinomadura madurae* as a subspecies designated *Actinomadura madurae* subspecies simaoensis.

TABLE III

Cultural Characteristics of LL-D42067 *Actinomadura madurae* subspecies *simaoensis* on ISP Morphological Media

| Agar Medium | Aerial Mycelium | Vegetative Mycelium | Soluble Pigment |
|---|---|---|---|
| Yeast extract, Malt extract (ISP 2) | White, sparse | Medium orange-brown-I53* | None |
| Inorganic Salts Starch (ISP 4) | Colorless | Colorless | None |
| Glucose Asparagine (ISP 5) | Colorless | Colorless | None |
| Oatmeal (ISP 3) | Sparse pinkish-white | Light orange-brown-I52* | None |

*I = ISCC Color charts

TABLE IV

Comparison of Carbohydrate Utilization Reactions of LL-D42067 With Related Actinomadura spp.

| Carbohydrate | LL-D42067 | *A. madurae* (a) | *A. verrucosopora* (a) (b) |
|---|---|---|---|
| L-arabinose | + | + | + |
| D-fructose | + | + | + |
| I-inositol | − | variable | variable |
| D-mannitol | + | + | + |
| raffinose | − | − | − |
| rhamnose | + | + | + |
| sucrose | + | + | + |
| D-xylose | + | + | + |

(a) Goodfellow, M., et al., J. Gen. Microbiol., 112:95–111 (1979).
(b) Nonomura, H. and O'Hara, Y., J. Ferm. Technol., 49:904–912 (1971).

TABLE V

Gordon Test Reactions of LL-D42067

| | LL-D42067 | *A. madurae* (Gordon Data*) |
|---|---|---|
| Degradation/Transformation of | | |
| Casein | + | +(98) |
| Xanthine | − | − |
| Hypoxanthine | + | +(98) |
| Tyrosine | + | +(91) |
| Adenine | − | − |
| Production of | | |
| Amylase | − | + |
| Gelatinase | + | + |
| Phosphatase | − | ND |
| Nitrate Reductase | + | +(98) |
| Urease | − | − |
| Esculinase | + | +(98) |
| Growth on/in | | |
| 5% Sodium Chloride | − | ND |
| Salicylate | − | ND |
| Lysozyme Broth | − | −(91) |
| Utilization | | |
| Acetate | + | + |
| Benzoate | − | −(94) |
| Citrate | − | +(83) |
| Lactate | + | ND |
| Malate | + | +(84) |
| Mucate | − | − |
| Oxalate | − | ND |
| Propionate | − | ND |
| Pyruvate | + | ND |
| Succinate | + | +(83) |
| Tartrate | − | − |
| Growth at | | |
| 10° C. | − | − |
| 45° C. | + | −(66) |
| 53° C. | − | − |
| Acid from | | |
| Adonitol | + | +(91) |
| Arabinose | + | + |
| Cellobiose | + | + |
| Dextrin | + | ND |
| Dulcitol | − | − |
| Erythritol | − | − |
| Fructose | + | ND |

TABLE V-continued

Gordon Test Reactions of LL-D42067

| | LL-D42067 | A. madurae (Gordon Data*) |
|---|---|---|
| Galactose | + | +(84) |
| Glucose | + | + |
| Glycerol | − | + |
| Inositol | − | +(60) |
| Lactose | − | +(55) |
| Maltose | − | +(53) |
| Mannitol | + | + |
| Mannose | + | +(94) |
| Melibiose | − | − |
| α-Methyl-D-glucoside | − | − |
| Raffinose | variable | − |
| Rhamnose | + | + |
| Salicin | + | ND |
| Sorbitol | − | − |
| Sucrose | + | ND |
| Trehalose | + | +(96) |
| Xylose | + | + |
| β-Methyl-D-xyloside | + | ND |

*Percentages of cultures showing reaction given in parentheses if not 100%.
ND = Not determined.

For the production of this new antibacterial and antiparasitic agent the present invention is not limited to this particular organism or to organisms fully answering the above growth and microscopic characteristics, which are given for illustrative purposes only. In fact, it is desired and intended to include the use of naturally-occurring mutants of this organism as well as induced mutants produced from this organism by various mutagenic means known to those skilled in the art such as exposure to nitrogen mustard, X-ray radiation, ultraviolet radiation, N'-methyl-N'-nitro-N-nitrosoguanidine, actinophages and the like. It is also desired and intended to include inter- and intraspecific genetic recombinants produced by genetic techniques known to those skilled in the art such as, for example, conjugation, transduction and genetic engineering techniques.

The in vitro antimicrobial spectrum of LL-D42067α was determined by the agar plate dilution method with Mueller-Hinton agar and an inoculum of each test organism of approximately $10^4$ colony forming units delivered by the Steers replicating device. The minimal inhibitory concentration (MIC) in mcg/ml was defined as the lowest concentration of LL-D42067α that inhibited visible growth after 18 hours incubation at 35° C.

The results, summarized in Table VI, show that LL-D42067α was active versus gram-positive bacteria and moderately active against yeasts.

TABLE VI

Antimicrobial Spectrum of LL-D42067α

| Test Organism | | MIC (mcg/ml) |
|---|---|---|
| *Staphylococcus aureus* | Smith | ≦0.06 |
| *Staphylococcus aureus* | LL #14 | ≦0.06 |
| *Staphylococcus aureus* | LL #27 | ≦0.06 |
| *Staphylococcus aureus* | LL #45 | ≦0.06 |
| *Staphylococcus aureus* | ATCC 25923 | ≦0.06 |
| *Staphylococcus epidermidis* | CMC-83-56 | ≦0.06 |
| *Staphylococcus epidermidis* | ATCC 12228 | ≦0.06 |
| *Streptococcus faecalis* | ATCC 29212 | ≦0.06 |
| *Streptococcus* (enterococcus sp) | OSU-75-1 | ≦0.06 |
| *Streptococcus* (enterococcus sp) | SM-77-15 | ≦0.06 |
| *Streptococcus mutans* | ATCC 27352 | ≦0.06 |
| *Streptococcus mutans* | BHI (b) | ≦0.06 |
| *Streptococcus sanguis* | G9B (a) | ≦0.06 |
| *Micrococcus luteus* | PC 1001 | ≦0.06 |
| *Bacillus subtilis* | ATCC 6633 | ≦0.06 |
| *Bacillus cereus* | LL #4 | ≦0.06 |
| *Candida albicans* | CA 300 | 256 |
| *Saccharomyces cerevisiae* | Y 15 | 32 |

TABLE VI-continued

Antimicrobial Spectrum of LL-D42067α

| Test Organism | | MIC (mcg/ml) |
|---|---|---|
| *Escherichia coli* | #311 | 512 |
| *Escherichia coli* | ATCC 25922 | 512 |
| *Klebsiella pneumoniae* | AD | 512 |
| *Proteus morganii* | K-79-25 | 512 |
| *Acinetobacter calcoaceticus* | Stfd-79-17 | 512 |

The antibiotic LL-D42067α derives utility from its antibacterial and antiparasitic activities. For example, the antibiotic may be used in the suppression of intestinal bacterial flora, as a topical antibacterial agent or antiseptic against gram-positive bacteria and as a general disinfectant for surfaces such as instruments. It may also be useful as an antiprotozoal agent in the treatment of malaria. In addition to its antimicrobial and antiparasitic activity LL-D42067α is effective as an anticoccidial agent in poultry. This utility is the subject of a copending application for United States Letters Patent.

In therapeutic use, the compound of this invention may be administered in the form of conventional pharmaceutical compositions appropriate for the intended use. Such compositions may be formulated so as to be suitable for oral or topical administration. The active ingredient may be combined in admixture with a non-toxic pharmaceutically acceptable carrier, which carrier may take a wide variety of forms depending on the form of preparation desired for administration, i.e., oral or topical.

GENERAL FERMENTATION CONDITIONS

Cultivation of *Actinomadura madurae* subspecies simaoensis NRRL 15734 may be carried out in a wide variety of liquid culture media. Media which are useful for the production of this novel antibiotic LL-D42067α include an assimilable source of carbon, such as dextrin, sucrose, molasses, glycerol, etc.; an assimilable source of nitrogen such as protein, protein hydrolysate, polypeptides, amino acids, corn steep liquor, etc.; and inorganic anions and cations, such as potassium, sodium, ammonium, calcium, sulfate, carbonate, phosphate, chloride, etc. Trace elements such as boron, molybdenum, copper, etc., are supplied as impurities of other constituents of the media. Aeration in tanks and bottles is supplied by forcing sterile air through or onto the surface of the fermenting medium. Further agitation in tanks is provided by a mechanical impeller. An antifoam agent such as silicone oil may be added as needed.

GENERAL PROCEDURE FOR THE ISOLATION OF LL-D42067α

The LL-D42067α antibiotic is recovered from the fermentation broth by filtration through diatomaceous earth, extracted into a solvent such as methylene chloride and purified by column chromatography on silica gel, using the system hexane:ethyl acetate (80:20) to remove unwanted fats and then methylene chloride:1% acetic acid in methanol (9:1) to give a crude product.

This crude LL-D42067α is then purified by high performance liquid chromatography on a reverse phase column using the system acetonitrile:water:acetic acid (600:400:0.28).

EXAMPLE 1

Inoculum Preparation

A typical medium used to grow the primary inoculum was prepared according to the following formula:

| | |
|---|---|
| Glucose | 1.0% |
| Dextrin | 2.0% |
| Yeast extract | 0.5% |
| N-Z Amine A ®[1] | 0.5% |
| Calcium carbonate | 0.1% |
| Water qs | 100% |

[[1]A pancreatic digest of casein, registered trademark of Sheffield Chemical, Norwich, New York]

This medium was adjusted to pH 7.2 and then sterilized. A 100 ml portion of this sterile medium, in a 500 ml flask, was inoculated with mycelial scrapings from an agar slant of *Actinomadura madurae* subspecies simaoensis NRRL 15734. The medium was then placed on a rotary shaker and agitated vigorously at 210 rpm for 48–72 hours at 28° C. This primary inoculum was then used to inoculate 12 liters of the same sterile medium which was then grown at 28° C. for 48 hours providing secondary inoculum.

EXAMPLE 2

A fermentation medium of the following formulation was prepared:

| | |
|---|---|
| Sucrose | 3.0% |
| Soy flour | 1.5% |
| Corn steep liquor | 0.5% |
| Calcium carbonate | 0.5% |
| Water qs | 100% |

The medium was sterilized and inoculated at the rate of 12 liters of secondary inoculum from Example 1 per 300 liters of medium. The fermentation was conducted at 28° C. with a sterile air flow of 200 liters per liter of mash per minute, agitation by an impeller operated at 230 rpm for 135–159 hours at which time the mash was harvested and filtered through diatomaceous earth.

EXAMPLE 3

Isolation of LL-D42067α

The fermentation filtrate from three fermentations, conducted as described in Example 2, were combined, making a total of 1800 liters at pH 7.5, and extracted with 900 liters of methylene chloride. The organic phase was concentrated in vacuo to give 84.1 g of residue.

A 75.2 g portion of this residue was suspended in 300 ml of hexane:ethyl acetate (80:20) and allowed to seep into a glass column (2 inches×20 inches) dry packed with silica gel. The column was eluted with a total of 4 liters of the same solvent mixture in order to remove fats and silicone oil and was then eluted with 4 liters of methylene chloride:1% acetic acid in methanol (9:1) collecting 15 ml fractions. The fractions were analyzed by thin-layer chromatography. Antibiotic LL-D42067α appeared visually as a yellow spot (Rf=0.5) with the same solvent system. Fractions 31–60, which contained most of the antibiotic, were pooled and concentrated in vacuo, giving 11.1 g of a red residue.

A 5.5 g portion of the above residue was fractionated by high performance liquid chromatography [Prep LC System-500, Prep PAK-500/C18 cartridge, acetonitrile:water:acetic acid (600:400:0.28), 100 ml/minute, 5.5 g/30 ml/injection]. Thirty 200 ml fractions were collected. Analytical high performance liquid chromatographic analysis of the fractions showed the major portion of LL-D42067α was in fraction 5. Fraction 5 was allowed to stand overnight. The resulting yellow crystals were collected by decanting off the mother liquor (which was saved), washing the crystals with the mobile phase and air drying, giving 11 mg of LL-D42067α as yellow crystals.

The mother liquor was concentrated by slow evaporation. The resulting precipitate was collected by centrifugation giving 377 mg of LL-D42067α as a yellow amorphous solid.

The analytical HPLC conditions were:

| | |
|---|---|
| Column: | μ Bondapak C18, 3.9 mm × 30 cm, Waters Associates |
| Mobile Phase: | acetonitrile:water:acetic acid (400:600:0.28) |
| Detector: | UV 254 nm and UV 365 nm, 0.2 AUFS |
| Flow Rate: | 1.0 ml/minute |
| Retention Volume of LL-D42067α: | 11.5 ml. |

We claim:
1. The compound designated as LL-D42067α, wherein the compound has:
   (a) the relative stereochemistry and structure:

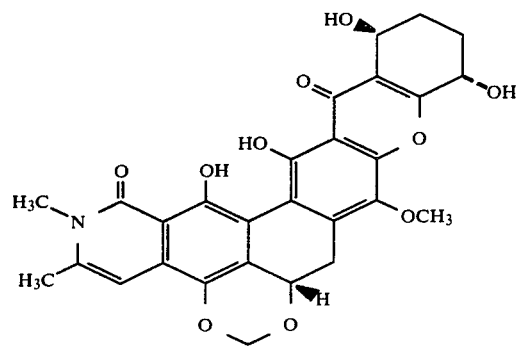

(b) a molecular weight of 535 (FAB-MS);
   (c) a molecular formula: $C_{28}H_{25}NO_{10}$;
   (d) a specific optical rotation: $[\alpha]_D^{26} = +836^\circ \to -40^\circ$ (C 0.3, DMF);
   (e) characteristic ultraviolet absorption spectra as shown in Figure I of the attached drawings;
   (f) a characteristic infrared absorption spectrum as shown in FIG. II of the attached drawings;
   (g) a characteristic proton nuclear magnetic resonance spectrum as shown in FIG. III of the attached drawings;
   (h) a characteristic carbon-13 nuclear magnetic resonance spectrum as shown in FIG. IV of the attached drawings with significant peaks at: 20.4; 25.4; 25.8; 29.0; 30.4; 58.5; 61.6; 63.3; 71.7; 90.4; 100.0; 109.2; 109.7; 111.0; 113.7; 119.0; 125.8; 126.6; 134.9; 135.3; 136.1; 141.3; 147.9; 151.1; 152.5; 165.4; 165.6; 182.3; and
   (i) a characteristic proton to carbon-13 chemical shift correlation as shown in Figure V of the attached drawings.

* * * * *